United States Patent [19]

Cosman

[11] Patent Number: 5,160,337

[45] Date of Patent: Nov. 3, 1992

[54] CURVED-SHAPED FLOOR STAND FOR USE WITH A LINEAR ACCELERATOR IN RADIOSURGERY

[76] Inventor: Eric R. Cosman, 872 Concord Ave., Belmont, Mass. 02178

[21] Appl. No.: 587,016

[22] Filed: Sep. 24, 1990

[51] Int. Cl.$^5$ .................... A61B 19/00; A61B 6/00; A61B 6/04

[52] U.S. Cl. .................... 606/130; 378/17; 378/209

[58] Field of Search .............. 606/130, 96, 97, 98; 378/64, 65, 17, 20, 208, 209

[56] References Cited

U.S. PATENT DOCUMENTS

| | | | |
|---|---|---|---|
| 4,583,537 | 4/1986 | Derechinsky | 606/130 |
| 4,608,977 | 9/1986 | Brown | 606/130 |
| 4,722,336 | 2/1988 | Kim | 606/130 |
| 4,750,487 | 6/1988 | Zanetti | 606/130 |

Primary Examiner—Michael Brown
Attorney, Agent, or Firm—Richard J. Birch

[57] ABSTRACT

This invention relates to a design of a floor stand structure to be used in conjunction with stereotactic radiosurgery or radiotherapy with a linear accelerator (LINAC). The floor stand is typically mounted on the floor bearing of the LINAC and rotates about a vertical axis. It has a contoured shape, which might be C-shaped, so that the gantry of the LINAC can swing by the floor stand in its lowest position. This is enabled by the contoured shape of the floor stand structure. The floor stand is used to stabilize the positioning of a patient's anatomy relative to the isocenter of the LINAC. It is typically attached to the rotating portion of the LINAC floor bearing, or could be self-standing with its own vertical bearing system to make it independent of the LINAC floor bearing.

6 Claims, 6 Drawing Sheets

CURVED-SHAPED FLOOR STAND FOR USE WITH A LINEAR ACCELERATOR IN RADIOSURGERY

BACKGROUND TO THE INVENTION

The use of a LINAC for external beam irradiation or stereotactic radiosurgery and radiotherapy is now commonly done. Some key references to this subject would be the articles by Winston and Lutz, Bova and Friedman, and brochures from Fischer company in Germany. A LINAC delivers a beam of photons through a collimated slit system. A schematic in FIG. 1 of a linear accelerator shows the basic degrees of freedom. There is a gantry 1 which rotates about horizontal axis 2 that is defined by the gantry bearing 3 anchored to the linear accelerator housing 6 which is anchored to the floor 7. The gantry can swing in an arc indicated by dashed line 5. The photon beam emerges from collimator 4 and aims at the target along the dashed line 8. The second principle structure of the LINAC is the couch 9, which is connected to the rotating floor bearing 10, and both of them rotate about the vertical axis 11. In use, the patient 21 lies on top of the movable superstructure 20 of the couch, and couch top 21 can move in three perpendicular directions to locate the anatomical target at the intersection of the two axes 11 and 22. That intersection 18 is referred to as the isocenter of the LINAC and is the point where all of the radiation converges for any couch position or any gantry position. The couch sweeps around the vertical axis along an arc indicated by 21, which is a horizontal plane.

Figure 1:
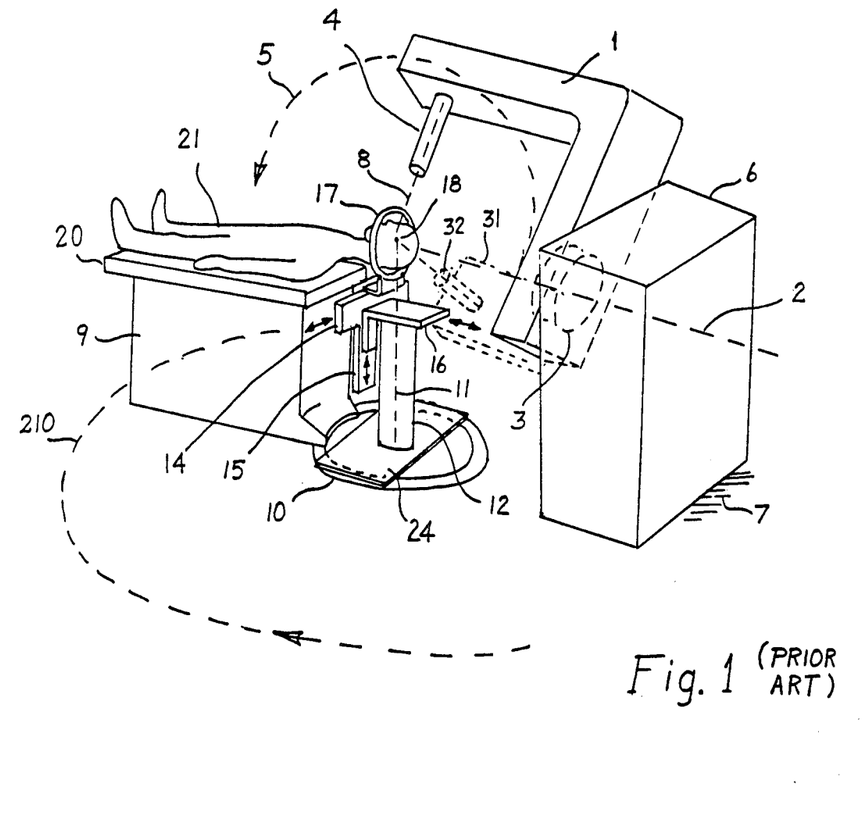
FIG. 1 shows a typical prior art arrangement of a LINAC with a floor stand mounted to the LINAC for stereotactic radiosurgery.

The concept of stereotactic radiosurgery is that the patient is fitted with a head ring 17 that is anchored to his skull. Various images are taken of his head and brain with the head ring 17 on, and targets within the head are located quantitatively by their Cartesian coordinates, refereed to as AP (anterior-posterior), lateral, and vertical directions relative to the ring 17. One of the common uses of the LINAC for stereotactic radiosurgery is the bombardment with the photons or X-rays from the LINAC of tumors or arterio-venous malformations (AVM's) in the brain. The coordinates of these targets relative to head ring 17 are known before the patient is put onto the LINAC from the above-mentioned image data. At present, there are two approaches to stereotactic radiosurgery and clamping of the patient to the couch. One is the couch-mounted arrangement typified by the Fischer brochure. Here the head ring 17 is fastened to a means that clamps to couch top 20. Thus the three orthogonal movements of the couch top would enable that the anatomical target can be moved to the isocenter 18; thereby, when the beam is turned on and various gantry and couch positions are assumed, the entering photon radiation from the LINAC is spread out over the intervening tissue and concentrated at the target, which is at the convergence point or isocenter of the LINAC. The second common approach is the floor stand mounted method typified by the papers of Winston and Lutz and of Friedman and Bova. In both of those cases a floor stand, like the one shown in FIG. 1, is mounted onto the rotating floor bearing 10 of the LINAC. This is usually done by some kind of a plate structure like 24 in FIG. 1. On top of the floor stand are the slide elements 14, 15, and 16 which enable the head of the floor stand to be translated in the three perpendicular directions: AP, lateral, and vertical. The top of the floor stand head is attached to the head ring 17 so that the head ring and the anatomical target are thus translated to the appropriate position so that the target is at the isocenter 18 of the LINAC.

The floor stand method has the advantage that the floor stand is a rigid coupling to the primary floor bearing of the LINAC. This means that as the couch turns, there is minimal variation in the accuracy of the isocenter positioning. The couch and the couch top may have a certain amount of sag or variability as the patients of different weights are loaded onto it and the couch is moved in its circular arc on the floor. Thus the floor stand positioning with its rigid fixation to the primary bearing represents an improvement in accuracy over the couch-mounted system mentioned above.

Figure 2:
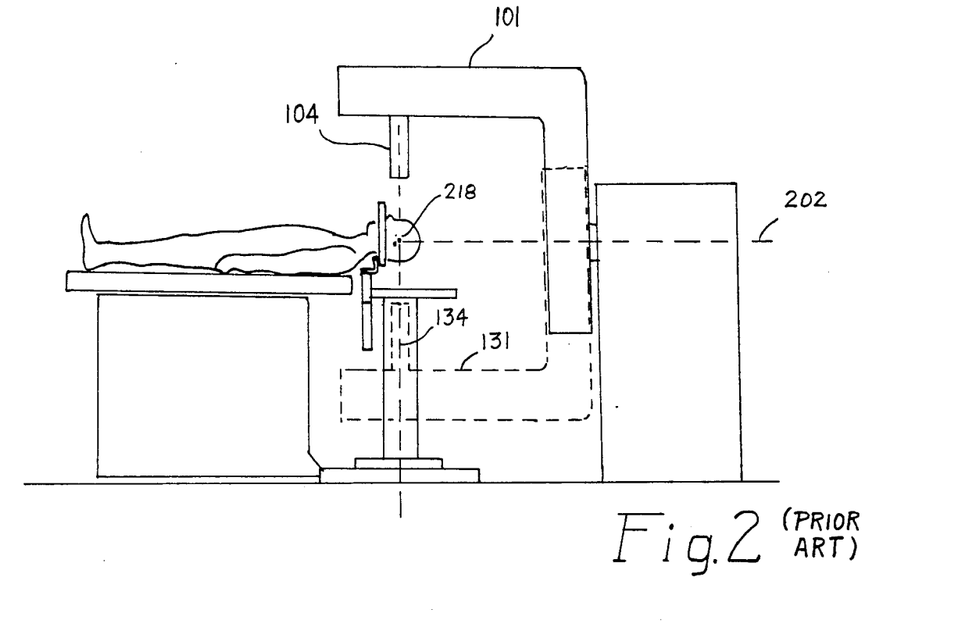
FIG. 2 is also prior art and shows another side elevation view of the same instrumentation as in FIG. 1.

One of the disadvantages of the floor stand-mounted system, as shown in FIG. 1 and FIG. 2, which are prior art, is that the floor stand post 12 and the head of the floor stand, represented by structures 14, 15, and 16, prevent the gantry 1 from swinging underneath the patient's head. This is illustrated by the dashed positioning of the gantry 31 and 32 in FIG. 1, and it also is illustrated by the upper position 101 and 104 in FIG. 2, as opposed to the lowest position 131 and 134 of the gantry and collimator, respectively. There are two severe difficulties with this limitation in the gantry movement. One is a safety consideration that if the gantry were to accidentally come around and strike the floor stand, it could knock the floor stand down with the patient attached to it, causing severe injury to the patient. A second consideration is that often one wishes to deliver the radiation in the upwardgoing beam position or in the lower orientation of the gantry. This is prevented by the floor stand configuration shown in FIGS. 1 and 2 and represents a limitation in the appropriate dosimetry that can be delivered for these procedures.

Thus, an objective of the present invention is to eliminate this restriction of the floor stand to gantry movement, and yet another objective of the present invention is to improve on the safety of such a floor-mounted floor stand device by preventing collision with the LINAC gantry.

DESCRIPTION OF THE PRESENT INVENTION

Figure 3:
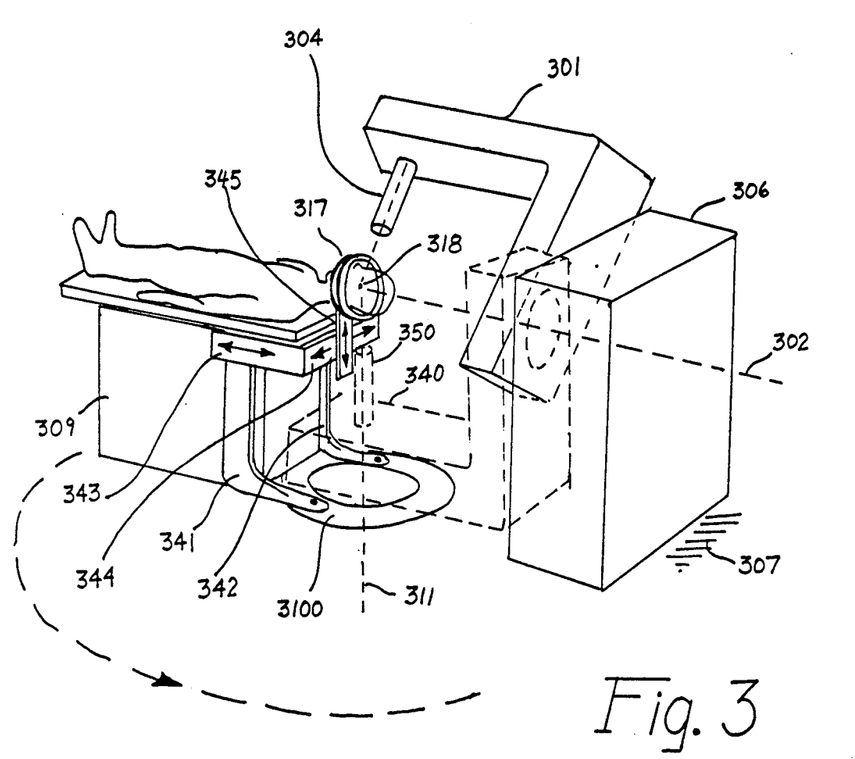
FIG. 3 shows an embodiment of the present invention with the curved-shaped floor stand in place relative to the LINAC.

Referring to FIG. 3, again we have the linear accelerator with its gantry 301 and horizontal axis 302 intersecting the vertical axis 311, which corresponds to the rotation axis of the couch 309. In the present invention, we see a floor stand which has a curved shape, or a shape which avoids the region around the axis 312 where the LINAC gantry 301 would swing. Note that the gantry position 340 in its lowest orientation is free to pass directly underneath the patient's head or the head ring 317, which is secured to the head. The particular embodiment of FIG. 3 is illustrated by the legs 341 and 342, which are secured to the rotating bearing 3100. The legs 341 and 342 curve upward to a vertical position which then connect to other elements 343, which move in a horizontal motion as indicated by the arrow. This in turn is connected to a further structure 344, which has a horizontal slide groove in it, further indicated by an arrow. Finally, there is the element 345, which moves in a vertical motion indicated by that arrow. Thus, the curved floor stand embodiment in FIG. 3 provides the same sort of Cartesian or rectilinear movements as the floor stand in FIG. 1, except now there is an open space for the gantry to pass to its lower configuration. The element 345 would be connected by adaption means to the head ring 317 so that the three coordinate slides would implement the translation of the head ring, and thus the patient's head, in space so that the anatomical target can be brought to the isocenter 318. The entire floor stand structure could be very rugged and actually provide a rigid mechanical basis for securing the head ring. Thus this design, as the design in FIG. 1, could be independent of the couch and thus independent of any variation or sloppiness in the construction of the couch. Notice that the gantry can now swing completely below so that the collimator in an upper hemisphere orientation, such as 304, or in a lower orientation, such as 350, can access the beam to the patient from above or below. This gives greater flexibility for entry beams and avoids the possibility of collision of the gantry with the floor stand.

Figure 4:
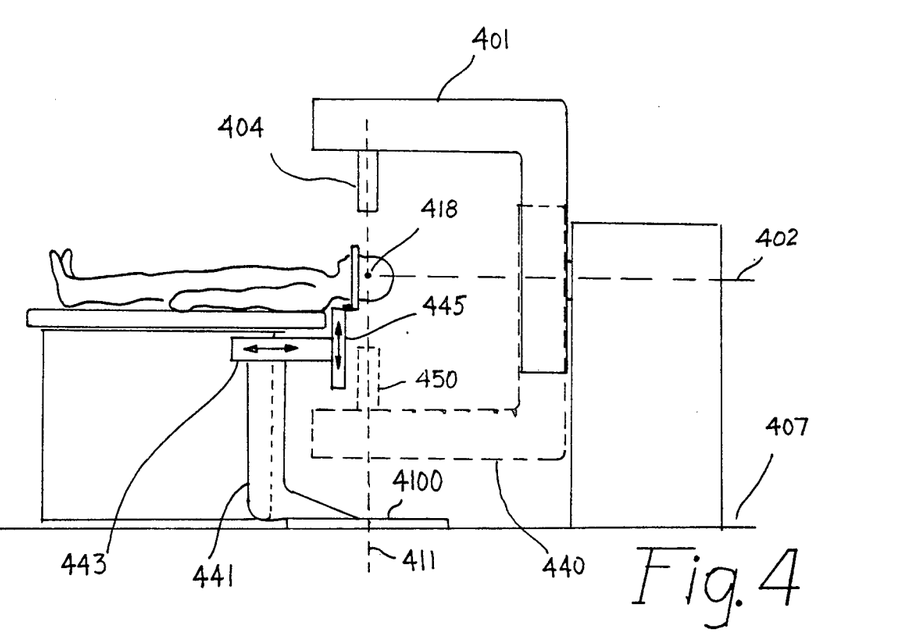
FIG. 4 shows a side elevation view of the present invention of FIG. 3, showing the greater degree of freedom of the gantry movement.

This is further illustrated in FIG. 4, which is the same embodiment of the present invention as FIG. 3 but shown in a side elevation view. Note that the gantry 401 and its collimator 404 in the upper position project the beam downward from above to the isocenter and thus target position 418. Because the C stand or curved stand elements 441, 443, and 445 have an overall curved configuration, they allow the gantry represented by the dashed lines 440 and its collimator 450 in their lowest position to be clear of the floor stand in the present invention.

FIGS. 3 and 4 illustrate one particular embodiment of this floor stand. There are clearly many others that could be devised. It is not necessary, for example, to have the two independent legs 341 and 342, but rather only one element of that nature might be used. There are also many ways of implementing the configuration for the three orthogonal Cartesian axis movements, which are illustrated by elements 343, 344, and 345.

One of the essential features of this invention is that it avoids collision with the gantry, which is illustrated in FIGS. 3 and 4. This is accomplished by the floor stand avoiding the region of the vertical axis. illustrated by dashed lines 311 and 411 in FIGS. 3 and 4, respectively. It is required that the support structure which rotates about the bearing axes 311 and 411 be deviant from that axis for a certain portion of the axis. The reason for this is that the gantry in its lower position, for example 440 in FIG. 4, must traverse and cut this axis 411 over a certain segment of the axis. Thus, another way of describing this floor stand is that it is a floor stand which rotates about the vertical axis 411 which is referred to frequently herein as the floor bearing axis, but it does not have to be restricted to the floor bearing) but does not coincide physically with that axis for a finite segment, that segment which the gantry traverses. The floor stand must therefore ride on some sort of bearing, as we have illustrated by bearing 4100 and 3100 in FIGS. 4 and 3, but that bearing does not have to be approximate to the floor 307 and 407. Those skilled in the art could conceive of other arrangements whereby such a floor stand could be attached to a bearing about axis 311 or 411 and still avoid the space of the gantry and collimator 440 and 450 as they swing beneath the patient.

Figure 5:
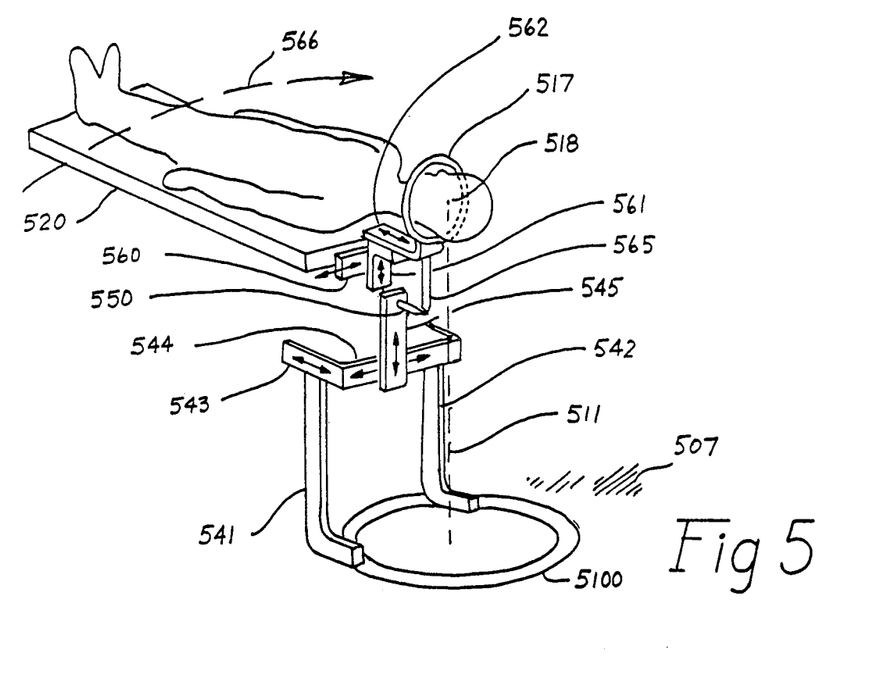
FIG. 5 shows yet another embodiment of the present invention, in this case using a curved-shaped floor stand in conjunction with a couch-mounted device, whereby the floor stand does not fasten directly to the couch-mounted head holder but acts as a reference positioning guide for it.
Figure 6:
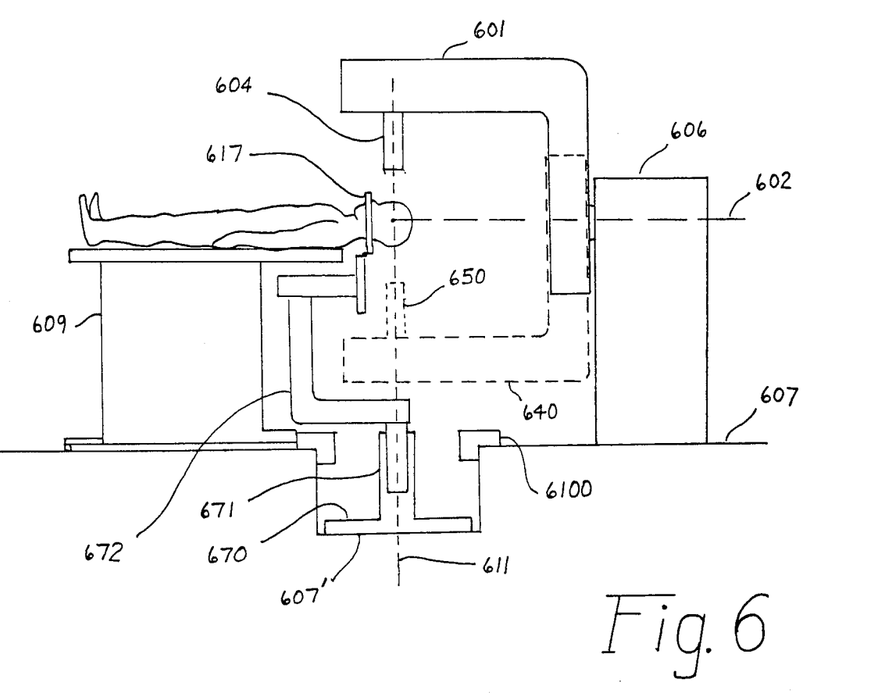
FIG. 6 shows a C-shaped curved floor stand in place where the floor stand is not mounted directly to the floor bearing as in FIGS. 3, 4, and 5, but is mounted to its own bearing that is independent of the couch LINAC bearing.

FIG. 5 is another embodiment of the present invention where the entire linear accelerator or LINAC is not shown in the future, but for simplicity only the floor bearing 5100 and the vertical axis corresponding to it 511. The concept in this drawing is that the floor stand does not necessarily have to be a rigid mechanical clamp of the patient or correspondingly the patient-connected head ring 517. The floor stand could act as a reference guide for the head ring or a stable reference relative to the vertical axis 511 or corresponding isocenter 518 so that the operator can determine at any time if there is variation of the head ring from its desired position and thus of the anatomy from the desired position relative to the isocenter 518. Again, we have analogous elements 541, 542, 543, 544, and 545 which provide orthogonal slide movements of a pointer in space illustrated by 550. This apparatus is not connected mechanically to the head ring. The head ring 517 is instead connected to the couch 520, so this arrangement could be described as a couch-mounted system. Onto the end of the couch are elements 560, 561, and 562, which provide verniated movements of the head ring 517 relative to the couch. Thus, in application the radiologist could move the head ring 517 in orthogonal directions to bring the isocenter 518 coincident with the anatomical target. This can be done with the orthogonal movements of the couch itself, and it is not required to have any such slide movements as shown in FIGS. 1, 2, 3, or 4. If the patient gets onto the couch, there may be a certain degree of sag which would require verniated or incremental movements of the head ring 517 to trim the ring back to proper isocenter orientation. These could be done by the vernier movements 560, 561, and 562. Of course these same movements could be used to provide the macroscopic positioning of the anatomical target to the isocenter 518 so that they could substitute for the movements of the floor stand slides in FIGS. 1 through 4, if one wanted. To illustrate how the floor stand in FIG. 5 could act as a nonmechanically coupled stabilizing element for the positioning of the patient, rather than a mechanical-coupled element such as in FIGS. 3 and 4, we have included for illustration an index rod 565 which is mechanically attached in a known way to head ring 517. The pointer 550 that is attached to the floor stand can be coincident with the point 565 when the proper alignment has been achieved between the head ring or equivalently the assembly 560, 561, and 562 to the isocenter. Supposing that the floor stand, which is a stable reference in space that moves around the vertical axis 511, can now act as stable reference point relative to the head ring and its attached assemblages. Now suppose that the head ring has been aligned relative to the isocenter. Now suppose also that the couch attachment 560, 561, and 562 have been aligned properly to the isocenter so that when the head ring and patient are placed on it the anatomy will be coincident with the isocenter. At this point, the adjustments on the couch-mounted adaptions and the head ring will be such that the two pointers 550 and 565 will be coincident. Now if the patient is set on the table, the table may sag and move. The two pointers will no longer meet, but one is assured that the floor stand pointer 550 has not moved in space, since it is independent of the couch and patient and is rigidly attached to a bearing around the vertical axis 511. At this point, small correction movements on the slides 560, 561, and 562 can be made to bring pointer 565 back into coincidence with pointer 550. Thus an incremental correction can be made to take out any variations relative to sag or variability of the couch relative to a known reference point relative to the rotation axis 511. This would be an illustration of how such a C-shaped or collision-free floor stand can be used as a mechanical reference but not necessarily a mechanical securing means for the patient attachment means. Similarly, the couch, when it traverses its circular arc, illustrated by the rotation dashed line 566, may have variations in it due to irregularities of the floor or irregularities in the couch itself. Thus, for each discrete couch setting the alignment, which may have been achieved for a different angle between 550 and 565, may no longer be valid. Again, small variations in the assembly 560, 561, and 562 can correct for these minor variations, always keeping the isocenter true and always referencing them to the known stable pointer 550, which is attached rigidly to the floor stand. By this type of incremental movements, one can trim out any small variations in the system that could give errors in the positioning of isocenter relative to anatomy. FIG. 6 shows another embodiment of the present invention which illustrates how the curved or collision-free floor stand can be mounted relative to an independent anchoring on the floor and an independent bearing so that it is now free from any variations in the standard floor bearing of the linear accelerator. To illustrate this, we have the gantry 601 and collimator 604 in its upper position which rotates around the horizontal axis 602. Again we have the vertical axis 611 about which the couch rotates. The floor is represented by 607, and a floor bearing or couch bearing is present 6100. The couch 609 is attached via the floor bearing and rotates about the vertical axis 611, as described before. In the event that the floor or couch bearing 6100 is unstable, one can achieve a stability of the independent, collision-free or curved-shaped floor stand by anchoring a bearing mount 670 to the floor 607' A bearing 671 provides rotation of the rest of the curved floor stand 672 about the vertical axis 611. Again, the rectilinear movements at the top of the curved floor stand 672 would apply and are attached to the head ring 617, as illustrated in previous figures. Also again, the gantry in its lowest position is indicated by the dashed structure 640 with its collimator pointing upward 650 to access the patient from below and shoot the beam up in the upward direction. The fact that the bearing 671 is independent of the couch bearing 6100 means that the obstruction-free floor stand 672 is now independent of couch sag due to patient weight, floor variations, and other matters which could give aberrations in the stability of the floor bearing 610 relative to the vertical axis 611.

FIGS. 3, 4, 5, and 6 are illustrations and embodiments of the general concept of a floor stand which is designed to provide a rotating reference means of mechanical nature around the vertical axis of rotation of the LINAC, and have such mechanical feature that the structure does not intersect the vertical axis over a segment of that axis to prevent collision or obstruction to the LINAC gantry as it swings near and through that vertical axis. This is unique to this present invention. As illustrated before, all other floor stands are coincident with the vertical axis and obstruct and represent a collision hazard relative to the gantry. By having a curved shape or having a deviation of the floor stand away from the axis over a segment of the axis, one prevents this.

There are other variations of this scheme which could be useful. For example, in FIG. 3 it is possible to have digitized, encoded, motor-drive or otherwise electronically controlled elements on the movement slides of the floor stand in a Cartesian direction 343, 344, and 345 so that these movements can be read out digitally or otherwise electronically monitored to help the operator realize where the positioning of the floor stand is at any time. It is also possible to apply feedback motor drives to these translation elements to take out any known variability or predetermined variability of the isocenter as a function of the bearing movements around the vertical axis or of the gantry movement around the horizontal axis. This could, therefore, be a feedback control system which stabilizes the position of the isocenter in space by this means. It is also possible in FIG. 5 that the relative position of the pointer 550, which is the stable pointer relative to the floor stand, could be referenced to the pointer 565, which may have variations in it. A detection system of the relative position of these pointers in Cartesian space could enable feedback control, for example, to the translation slides 560, 561, and 562 so that the corrections can be made automatically to any deviations. This too would enable stability or correction of variations in isocenter position.

It is clear from FIG. 3 that the gantry 301 will not obstruct or collide with the couch or the floor stand when the gantry is in its lowest position, that is, with the beam pointing straight up, before the couch position as shown in FIG. 3 and also in FIG. 4. Of course, if the couch position were rotated 90°, the gantry would collide not only with the couch but also with the floor stand. So what is intended in this patent is that the gantry will not collide with the couch or the floor stand in certain angular positions of the floor stand. In an angular position like shown in FIGS. 3 and 4, this will obviously be the case. That is to say that when the gantry swings down and the gantry intercepts the vertical axis 311 in FIG. 3, it will not collide with the floor stand structure as shown in FIG. 3. Therefore there is a range of angular couch positions for which the gantry will not collide with the floor stand, or indeed the couch, for all positions of the gantry or at least for the position where the gantry is coincident with the vertical axis 311. Naturally, when the gantry is above the vertical axis, such as in position 401 in FIG. 4, it is not colliding with the floor stand in any case, but when it is in the lower position, such as FIG. 440 and FIG. 4, then it will also be free of the floor stand. It is also implicit in the embodiment of FIGS. 3 and 4 that the floor stand will rotate in synchronism in terms of angle with the floor stand about vertical axis 311. This is easily arranged in FIG. 3 and 4 since the floor stand is actually attached mechanically to the same floor bearing 3100 and 4100 that the couch is. In FIG. 6 where the floor stand bearing is independent of the couch bearing, an index tongue, for example, could ensure that the angular position of both the floor stand and the couch are equal at all times. This takes out any angular uncertainty, and it would only be the stability against other variations of the couch, such as sag under patient's weight or variations because of irregular floors, that the floor stand would be stabilizing against.

It is within the scope of this patent that any such obstruction-free or collision-free floor stand device could be used in any of these contexts or objectives. The objective would include mechanical securing to the patient attachment means for direct mechanical stabilization, reference indicators in space to provide information on position deviations of the patient attachment means relative to the vertical axis, or cooperatively coupled electronic and readout means to provide error feedback and position control elements to correct for any known or measured deviations of the patient position relative to the stable vertical axis.

It is possible to put on electronic encoders and motor drives on the translation elements shown in FIG. 5, either for the floor stand 543, 544. or 545 or for the table mounted elements 560, 561, and 562. In this way, automatic digital readout and feedback control to a computer system or other electronics could be used to trim in the position of the patient's head ring dependent on perturbations on known variations of the couch as it rotates around the vertical axis or the gantry as it rotates around the horizontal axis. Thus, electronically controlling the feedback between pointers 550 and 545 is possible and also automatic positioning of the patient electronically can be done by encoders, either on the apparatus in FIG. 5 or the apparatus in FIG. 3, that is on the Cartesian or translation slides in either one of those figures. This is also claimed as part of the present invention.

There are many variations in design and embodiment which can be thought of by those skilled in the art in such mechanical devices. It is the intention that this patent shall encompass such variations. Variation in the topology in exact arrangement of the shape of the floor stand to avoid a segment of the vertical axis which would be intercepted by the gantry to prevent collision would be included in the scope of this patent. Particular configurations of the floor stand, implementation of slides of movement to the floor stand are again obvious variations that will be included in the scope of this patent.

Having described the intention by the above illustration, what I would wish to secure by U.S. Letters Patent are the following claims:

1. A floor stand for a linear accelerator that has a base that is mounted on a floor and a rotatable gantry, said floor stand adapted to be collision-free relative to the gantry of said linear accelerator which rotates about a horizontal axis defined by said linear accelerator, said linear accelerator having a vertical axis around which a patient couch rotates, said patient couch being designed to support a patient during external irradiation by said linear accelerator through said linear accelerator gantry, said patient and said patient couch rotating about a couch bearing whose axis is said vertical axis and said couch bearing being fixed relative to the base of said linear accelerator, said vertical axis and said horizontal axis being arranged to intersect at the isocenter of said linear accelerator said patient having patient index which is fixed relative to said patient's body and provides a stereotactic reference base relative to said patient's anatomy, and said patient index position can be determined relative to said linear accelerator and said linear accelerator isocenter, so that an anatomical target in said patient's body can be determined by imaging to be in a known position relative to said patient index and thus can be positioned at said linear accelerator isocenter, said floor stand comprising:

a floor stand element attached to a floor stand bearing which is attached to said floor and whose axis is the same as said vertical axis, so that said floor stand element rotates also about said vertical axis and in the same angular orientation as said patient couch rotates about said vertical axis, said floor stand element, therefore, being a stable, independent reference object relative to said linear accelerator isocenter and said vertical axis when said floor stand element and said patient couch are in the same angular rotation position about said vertical axis, so that said patient index and said anatomical target can be positioned stably relative to said floor stand element and thus to said linear accelerator isocenter independent of variations of said patient couch position with patient loading or rotational orientation due to possible perturbations of the couch around its couch bearing, said floor stand element having a collision-free portion which is spatially separated from said vertical axis over a portion of said vertical axis, so that said gantry in its rotational variation about said horizontal axis of said linear accelerator will not collide with said floor stand element when said gantry position intercepts said vertical axis for at least some rotational positions of said floor stand element about said vertical axis.

2. The floor stand of claim 1 wherein the floor stand bearing is the same as the patient couch bearing and thus the floor stand element is mounted directly to the patient couch bearing.

3. The apparatus of claim 1 wherein said collision-free portion of said floor stand element comprises a contoured structure portion of said floor stand which deviates from said vertical axis over said portion of said vertical axis so as to avoid collision of said gantry with said floor stand when said gantry passes through said vertical axis for certain angular orientations of said floor stand and said couch around said vertical axis.

4. A floor stand system for a linear accelerator that has a base that is mounted on a floor and a rotatable gantry, said floor stand adapted to be collision-free relative to the gantry of said linear accelerator which rotates about a horizontal axis defined by said linear accelerator, said linear accelerator having a vertical axis around which a patient couch rotates, said patient couch being designed to support a patient during external irradiation by said linear accelerator through said linear accelerator gantry, said patient and said patient couch rotating about a couch bearing whose axis is said vertical axis and said couch bearing being fixed relative to the base of said linear accelerator, said vertical axis and said horizontal axis being arranged to intersect at the isocenter of said linear accelerator, said floor stand system comprising:

a patient index means which is fixed relative to said patient's body and provides a stereotactic reference base relative to said patient's anatomy, and said patient index means position can be determined relative to said linear accelerator and said linear accelerator isocenter, so that an anatomical target in said patient's body can be determined by imaging to be in a known position relative to said patient index means and thus can be positioned at said linear accelerator isocenter;

a floor stand element attached to a floor stand bearing which is attached to said floor and whose axis is the same as said vertical axis, so that said floor stand element rotates also about said vertical axis and in the same angular orientation as said patient couch rotates about said vertical axis, said floor stand element, therefore, being a stable, independent reference object relative to said linear accelerator isocenter and said vertical axis when said floor stand element and said patient couch are in the same angular rotation position about said vertical axis, so that said patient index means and said anatomical target can be positioned stably relative to said floor stand element and thus to said linear accelerator isocenter independent of variations of said patient couch position with patient loading or rotational orientation due to possible perturbations of the couch around its couch bearing, said floor stand element having a collision-free portion which is spatially separated from said vertical axis over a portion of said vertical axis, so that said gantry in its rotational variation about said horizontal axis of said linear accelerator will not collide with said floor stand element when said gantry position intercepts said vertical axis for at least some rotational positions of said floor stand element about said vertical axis.

5. The floor stand system of claim 4 wherein said patient index means comprises a mechanical patient fixation means attached to said patient's body and wherein said floor stand element is adapted to attach mechanically to said patient fixation means, so that said floor stand mechanically stabilizes said patient fixation means and thus said anatomical target relative to said linear accelerator isocenter.

6. The floor stand system of claim 4 wherein said patient index means comprises a mechanical patient fixation means attached to said patient's body and further includes a first index means, and said floor stand element includes a second index means whereby the relative position of said first and said second index means is an indication of the relative position of said anatomical target to said linear accelerator isocenter for various couch positions and patient variations on said couch and whereby said anatomical target can be trimmed into coincidence with said linear accelerator isocenter by moving said patient fixation means and thus said patient's anatomy so as to bring said first index means into coincidence with said second index means.

* * * * *